(12) United States Patent
Kloti

(10) Patent No.: US 6,399,857 B1
(45) Date of Patent: Jun. 4, 2002

(54) MODIFIED NUCLEOTIDE SEQUENCE ENCODING A LEXA DNA BINDING DOMAIN OPTIMIZED FOR ARABIDOPSIS SPECIES

(75) Inventor: Andreas S. Kloti, Durham, NC (US)

(73) Assignee: Paradigm Genetics, Inc.

( * ) Notice: Subject to any disclaimer, the term of this patent is extended or adjusted under 35 U.S.C. 154(b) by 0 days.

(21) Appl. No.: 09/401,171

(22) Filed: Sep. 22, 1999

(51) Int. Cl.$^7$ .......................... C12N 15/31; C12N 5/04; C12N 15/82; A01H 5/00; A01H 5/10
(52) U.S. Cl. .................... 800/278; 435/419; 435/320.1; 435/468; 536/23.7; 800/298; 800/317
(58) Field of Search .................... 435/410, 419, 435/69.1, 320.1, 468, 455; 536/23.6, 23.7; 800/278, 295, 298, 317

(56) References Cited

U.S. PATENT DOCUMENTS

| | | | |
|---|---|---|---|
| 5,380,831 A | 1/1995 | Adang et al. | 536/23.71 |
| 5,436,391 A | 7/1995 | Fujimoto et al. | 800/278 |
| 5,500,365 A | 3/1996 | Fischhoff et al. | 536/23.6 |
| 5,689,052 A | 11/1997 | Brown et al. | 536/23.6 |
| 5,877,306 A | 3/1999 | Cornelissen et al. | 536/23.6 |

OTHER PUBLICATIONS

Horli, et al, "Nucleotide Sequence of the lexA Gene of *E. Coli*" Mar. 1981, Cell vol. 23, pp. 689–697.*
Brent et al, "The lexA gene product represses its own promoter", Apr. 1980, Proc. Natl, Acad. Sci., vol. 77, No. 4, pp. 1932–1936.*
Brent et al, "A Eukaryotic Transcriptional Activator Bearing the DNA Specificity of a Prokaryotic Repressor", Dec. 1985 (part 2), Cell. vol. 43, pp. 729–736.*
Sharp et al., Codon Usage in regulatory genes in *Escherichia coli* does not reflect selection for 'rare' codons, Nucleic Acids Res, 14(19):7737–7749 Oct. 1986.
McKnight et al., Binding of the virion protein mediating alpha gene induction in herpes simplex virus 1–infected cells to its cis site requires cellular proteins, Proc Natl Acad Sci, 84(20):7061–7065 Oct. 1987, Abstract.
Ma et al., Deletion analysis of GAL4 defines two transcriptional activating segments, Cell, 48(5):847–853 Mar. 1987, Abstract.
Brent et al., A Eukaryotic Transcriptional Activator Bearing the DNA Specificity of a Prokaryotic Repressor, Cell, 43:729–736, Dec. 1985.
Bennetzen, et al., Codon selection in yeast, J Biol Chem, 257(6):3026–3031 Mar. 1982, Abstract.
Campbell et al., Codon Usage in Higher Plants, Green Algae, and Cyanobacteria, Plant Physiology, 92:1–11(1990).
Curran, et al., Fos and Jun: the AP–1 connection, Cell, 55(4):395–397 Nov. 1988, Abstract.
Keegan et al., Separation of DNA binding from the transcription–activating function of a eukaryotic regulatory protein, Science 231 (4739):699–704 Feb. 1986, Abstract.

* cited by examiner

*Primary Examiner*—Amy J. Nelson
*Assistant Examiner*—Ashwin D. Mehta
(74) *Attorney, Agent, or Firm*—Laura L. Kiefer; Tomothy G. Hofmeyer; Deborah H. Spencer

(57) ABSTRACT

A synthetic nucleotide sequence encodes the LexA DNA binding domain, the nucleotide sequence having been modified to bring the codon usage in conformity with the preferred codon usage of *Arabidopsis thaliana*. The preferred sequence of the gene is provided as SEQ ID NO:1. DNA constructs, transformed host cells and transgenic plants comprising the synthetic nucleotide sequence are also provided.

25 Claims, 3 Drawing Sheets

Figure 3:
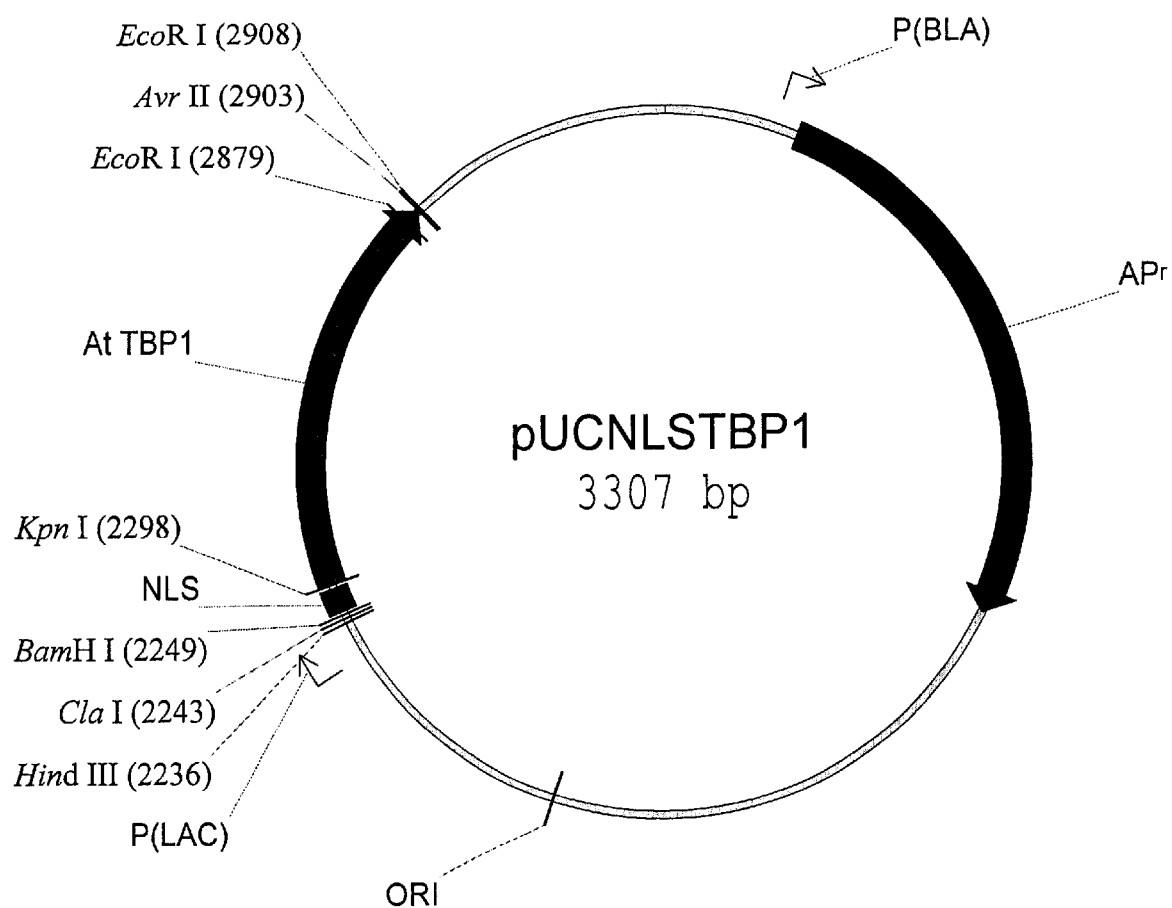

*DNA binding domain of LexA, codon optimized for Arabidopsis thaliana*

**LexA DNA binding domain DNA sequence, with codon usage adapted to *Arabidopsis thaliana***

ATGAAGGCTCTTACCGCTAGACAGCAGGAGGTTTCGATCTTATCAGAGATCACATCTCAGACCGG
AATGCCACCAACCAGAGAGCTGAGATCGCTCAGAGACTTGGATTCAGAGATCTCCAAACGCTGAGGAG
CACCTTAAGGCTCTGCTAGAAAGGGAGTTATCGAGATCGTTTCTGGAGCTTCTAGAGGAATCAGACT
TCTTCAGGAGGAGGAGGGACTTCCACTTGTTGGAAGAGTTGCTGCTGGAGAG [SEQ ID NO:1]

LexA DNA binding domain sequence, translated into amino acids:

Met-Lys-Ala-Leu-Thr-Ala-Arg-Gln-Gln-Glu-Val-Phe-Asp-Leu-Ile-Arg-Asp-His-Ile-Ser-Gln-Thr-Gly-Met-Pro-
Pro-Thr-Arg-Ala-Glu-Ile-Ala-Gln-Arg-Leu-Gly-Phe-Arg-Ser-Pro-Asn-Ala-Ala-Glu-His-Leu-Lys-Ala-Leu-
Ala-Arg-Lys-Gly-Val-Ile-Glu-Ile-Val-Ser-Gly-Ala-Ser-Arg-Gly-Ile-Arg-Leu-Leu-Gln-Glu-Glu-Glu-Gly-Leu-
Pro-Leu-Val-Gly-Arg-Val-Ala-Ala-Gly-Glu [SEQ ID NO:2]

*FIG.1*

AGCTTCATATGAAGGCTCTTACCGCTAGACAGCAGGAGGTTTCGATCTTATCAGAGATCACATCTCT
CAGACCCGGAATGCCACCAACCAGA [SEQ ID NO: 3]

GCTGAGATCGCTCAGAGAGACTTGGATTCAGATCTCCAAACGCTGCTGAGGAGCACCTTAAGGCTCTTG
CTAGAAAGGGAGTTATCGAGATC [SEQ ID NO:4]

GTTTCTGGAGCTTCTAGAGGAATCAGACTTCTTCAGGAGGAGGAGGAGGACTCCACTGTTGGAA
GAGTTGCTGCTGGAGAGG [SEQ ID NO:5]

ATCTCTGATAAGATCGAAAACCCTCCTGCTGTCTAGCGGGTAAGAGCCTTCATATGA [SEQ ID NO:6]

CTCAGCAGCGGTTTGGAGATCTGAATCCAAGTCTCTGAGCGATCTCAGCTCTGGTGTGGCATTCCGG
TCTGAGAGATGTG [SEQ ID NO:7]

CTCCTGAAGAAGTCTCTGATTCCCTCTAGAAGCTCCAGAAACGATCTCGATAACTCCCTTTCTAGCAAGAG
CCTTAAGGTGCTC [SEQ ID NO:8]

GATCCCTCTCCAGCAGCAACTCTTCCAACAAGTGGAAGTCCCCTCCCTC [SEQ ID NO:9]

CATACTGTATGAGCATACAG [SEQ ID NO:10]

FIG. 2

SEQUENCE LISTING

<160> NUMBER OF SEQ ID NOS: 11

<210> SEQ ID NO 1
<211> LENGTH: 258
<212> TYPE: DNA
<213> ORGANISM: Artificial Sequence
<220> FEATURE:
<223> OTHER INFORMATION: LexA DNA binding domai n of E. coli using
      Arabidopsis-optimized codons
<221> NAME/KEY: CDS
<222> LOCATION: (1)...(258)
<223> OTHER INFORMATION: LexA DNA binding domai n of E. coli

<400> SEQUENCE: 1

```
atg aag gct ctt acc gct aga cag cag gag g tt ttc gat ctt atc aga      48
Met Lys Ala Leu Thr Ala Arg Gln Gln Glu V al Phe Asp Leu Ile Arg
 1               5                  10                  15 gat cac atc tct cag acc gga atg cca cca a cc aga gct gag atc gct      96
Asp His Ile Ser Gln Thr Gly Met Pro Pro T hr Arg Ala Glu Ile Ala
             20                  25                  30 cag aga ctt gga ttc aga tct cca aac gct g ct gag gag cac ctt aag     144
Gln Arg Leu Gly Phe Arg Ser Pro Asn Ala A la Glu Glu His Leu Lys
         35                  40                  45 gct ctt gct aga aag gga gtt atc gag atc g tt tct gga gct tct aga     192
Ala Leu Ala Arg Lys Gly Val Ile Glu Ile V al Ser Gly Ala Ser Arg
     50                  55                  60 gga atc aga ctt ctt cag gag gag gag gag g ga ctt cca ctt gtt gga     240
Gly Ile Arg Leu Leu Gln Glu Glu Glu Glu G ly Leu Pro Leu Val Gly
 65                  70                  75                  80 aga gtt gct gct gga gag                                              258
Arg Val Ala Ala Gly Glu
                 85
```

<210> SEQ ID NO 2
<211> LENGTH: 86
<212> TYPE: PRT
<213> ORGANISM: Artificial Sequence
<220> FEATURE:
<223> OTHER INFORMATION: LexA DNA binding domai n of E. coli using Arabidopsis-optimized codons

<400> SEQUENCE: 2

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu
                85

<210> SEQ ID NO 3
<211> LENGTH: 92
<212> TYPE: DNA
<213> ORGANISM: Artificial Sequence
<220> FEATURE:
<223> OTHER INFORMATION: oligonucleotide

<400> SEQUENCE: 3
agcttcatat gaaggctctt accgctagac agcaggaggt tttcgatctt a tcagagatc      60 acatctctca gaccggaatg ccaccaacca ga                                     92

<210> SEQ ID NO 4
<211> LENGTH: 90
<212> TYPE: DNA
<213> ORGANISM: Artificial Sequence
<220> FEATURE:
<223> OTHER INFORMATION: oligonucleotide

<400> SEQUENCE: 4
gctgagatcg ctcagagact tggattcaga tctccaaacg ctgctgagga g caccttaag      60 gctcttgcta gaaagggagt tatcgagatc                                        90

<210> SEQ ID NO 5
<211> LENGTH: 85
<212> TYPE: DNA
<213> ORGANISM: Artificial Sequence
<220> FEATURE:
<223> OTHER INFORMATION: oligonucleotide

<400> SEQUENCE: 5
gtttctggag cttctagagg aatcagactt cttcaggagg aggaggaggg a cttccactt      60 gttggaagag ttgctgctgg agagg                                             85

<210> SEQ ID NO 6
<211> LENGTH: 55
<212> TYPE: DNA
<213> ORGANISM: Artificial Sequence
<220> FEATURE:
<223> OTHER INFORMATION: oligonucleotide

<400> SEQUENCE: 6
atctctgata agatcgaaaa cctcctgctg tctagcggta agagccttca t atga           55

<210> SEQ ID NO 7
<211> LENGTH: 81

```
<212> TYPE: DNA
<213> ORGANISM: Artificial Sequence
<220> FEATURE:
<223> OTHER INFORMATION: oligonucleotide

<400> SEQUENCE: 7
ctcagcagcg tttggagatc tgaatccaag tctctgagcg atctcagctc t ggttggtgg      60 cattccggtc tgagagatgt g                                                 81

<210> SEQ ID NO 8
<211> LENGTH: 81
<212> TYPE: DNA
<213> ORGANISM: Artificial Sequence
<220> FEATURE:
<223> OTHER INFORMATION: oligonucleotide

<400> SEQUENCE: 8
ctcctgaaga agtctgattc ctctagaagc tccagaaacg atctcgataa c tccctttct      60 agcaagagcc ttaaggtgct c                                                 81

<210> SEQ ID NO 9
<211> LENGTH: 51
<212> TYPE: DNA
<213> ORGANISM: Artificial Sequence
<220> FEATURE:
<223> OTHER INFORMATION: oligonucleotide

<400> SEQUENCE: 9
gatccctctc cagcagcaac tcttccaaca agtggaagtc cctccctcct c                51

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
catactgtat gagcatacag                                                   20

<210> SEQ ID NO 11
<211> LENGTH: 3307
<212> TYPE: DNA
<213> ORGANISM: Artificial Sequence
<220> FEATURE:
<223> OTHER INFORMATION: cloning vector

<400> SEQUENCE: 11
gacgaaaggg cctcgtgata cgcctatttt tataggttaa tgtcatgata a taatggttt      60 cttagacgtc aggtggcact tttcggggaa atgtgcgcgg aaccctatt t gtttatttt     120 tctaaataca ttcaaatatg tatccgctca tgagacaata accctgataa a tgcttcaat    180 aatattgaaa aaggaagagt atgagtattc aacatttccg tgtcgccctt a ttcccttt     240 ttgcggcatt ttgccttcct gttttgctc acccagaaac gctggtgaaa g taaaagatg     300 ctgaagatca gttgggtgca cgagtgggtt acatcgaact ggatctcaac a gcggtaaga    360 tccttgagag ttttcgcccc gaagaacgtt ttccaatgat gagcactttt a aagttctgc    420 tatgtggcgc ggtattatcc cgtattgacg ccgggcaaga gcaactcggt c gccgcatac    480 actattctca gaatgacttg gttgagtact caccagtcac agaaaagcat c ttacggatg    540 gcatgacagt aagagaatta tgcagtgctg ccataaccat gagtgataac a ctgcggcca    600
```

-continued

| | |
|---|---|
| acttacttct gacaacgatc ggaggaccga aggagctaac cgcttttttg c acaacatgg | 660 |
| gggatcatgt aactcgcctt gatcgttggg aaccggagct gaatgaagcc a taccaaacg | 720 |
| acgagcgtga caccacgatg cctgtagcaa tggcaacaac gttgcgcaaa c tattaactg | 780 |
| gcgaactact tactctagct tcccggcaac aattaataga ctggatggag g cggataaag | 840 |
| ttgcaggacc acttctgcgc tcggcccttc cggctggctg gtttattgct g ataaatctg | 900 |
| gagccggtga gcgtgggtct cgcggtatca ttgcagcact ggggccagat g gtaagccct | 960 |
| cccgtatcgt agtatctac acgacgggga gtcaggcaac tatggatgaa c gaaatagac | 1020 |
| agatcgctga gataggtgcc tcactgatta agcattggta actgtcagac c aagtttact | 1080 |
| catatatact ttagattgat ttaaaacttc atttttaatt taaaaggatc t aggtgaaga | 1140 |
| tcctttttga taatctcatg accaaaatcc cttaacgtga gttttcgttc c actgagcgt | 1200 |
| cagacccgt agaaaagatc aaaggatctt cttgagatcc ttttttttctg c gcgtaatct | 1260 |
| gctgcttgca aacaaaaaaa ccaccgctac cagcggtggt ttgtttgccg g atcaagagc | 1320 |
| taccaactct ttttccgaag gtaactggct tcagcagagc gcagatacca a atactgtcc | 1380 |
| ttctagtgta gccgtagtta ggccaccact tcaagaactc tgtagcaccg c ctacatacc | 1440 |
| tcgctctgct aatcctgtta ccagtggctg ctgccagtgg cgataagtcg t gtcttaccg | 1500 |
| ggttggactc aagacgatag ttaccggata aggcgcagcg gtcgggctga a cggggggtt | 1560 |
| cgtgcacaca gcccagcttg gagcgaacga cctacaccga actgagatac c tacagcgtg | 1620 |
| agctatgaga aagcgccacg cttcccgaag ggagaaaggc ggacaggtat c cggtaagcg | 1680 |
| gcagggtcgg aacaggagag cgcacgaggg agcttccagg gggaaacgcc t ggtatcttt | 1740 |
| atagtcctgt cgggtttcgc cacctctgac ttgagcgtcg attttttgtga t gctcgtcag | 1800 |
| gggggcggag cctatggaaa aacgccagca acgcggcctt tttacggttc c tggccttt | 1860 |
| gctggccttt tgctcacatg ttctttcctg cgttatcccc tgattctgtg g ataaccgta | 1920 |
| ttaccgcctt tgagtgagct gataccgctc gccgcagccg aacgaccgag c gcagcgagt | 1980 |
| cagtgagcga ggaagcggaa gagcgcccaa tacgcaaacc gcctctcccc g cgcgttggc | 2040 |
| cgattcatta atgcagctgg cacgacaggt ttcccgactg gaaagcgggc a gtgagcgca | 2100 |
| acgcaattaa tgtgagttag ctcactcatt aggcaccccca ggctttacac t ttatgcttc | 2160 |
| cggctcgtat gttgtgtgga attgtgagcg gataacaatt tcacacagga a acagctatg | 2220 |
| accatgatta cgccaagctt atcgatcgga tccgctcttg ctccaaagaa g aagagaaag | 2280 |
| gttgctcttg ctggtaccat gactgatcaa ggattggaag ggagtaatcc a gttgatctt | 2340 |
| agcaagcatc cttcagggat tgttcctact cttcaaaaca ttgtctccac g gtgaactta | 2400 |
| gactgcaagc tagatcttaa agccatagct ttgcaggctc ggaatgctga a tataatccc | 2460 |
| aagcgttttg ctgcggtgat aatgaggatc agagaaccga agactacagc a ttaatattc | 2520 |
| gcctcaggga aaatggtctg tactggagct aagagcgagg acttttcgaa g atggctgct | 2580 |
| agaaagtatg ctaggattgt gcagaaattg ggattccctg caaaattcaa g gatttcaag | 2640 |
| attcagaata ttgtaggttc ttgtgatgtc aaattcccta taagacttga a ggtcttgct | 2700 |
| tactctcacg ctgctttctc aagttatgag cccgagctct cccagggct g atttatagg | 2760 |
| atgaaagtcc caaaaatcgt ccttctaatc tttgtctctg ggaagatcgt a ataacagga | 2820 |
| gccaagatga gagatgagac ctacaaagcc tttgagaata tacccccgt g ctctcggaa | 2880 |
| ttcagaaaga tacagcaata gcctaggaat tcactggccg tcgttttaca a cgtcgtgac | 2940 |
| tgggaaaacc ctggcgttac ccaacttaat cgccttgcag cacatccccc t ttcgccagc | 3000 |

-continued

```
tggcgtaata gcgaagaggc ccgcaccgat cgcccttccc aacagttgcg c agcctgaat    3060 ggcgaatggc gcctgatgcg gtattttctc cttacgcatc tgtgcggtat t tcacaccgc    3120 atatggtgca ctctcagtac aatctgctct gatgccgcat agttaagcca g ccccgacac    3180 ccgccaacac ccgctgacgc gccctgacgg gcttgtctgc tcccggcatc c gcttacaga    3240 caagctgtga ccgtctccgg gagctgcatg tgtcagaggt tttcaccgtc a tcaccgaaa    3300 cgcgcga                                                              3307
```

MODIFIED NUCLEOTIDE SEQUENCE ENCODING A LEXA DNA BINDING DOMAIN OPTIMIZED FOR ARABIDOPSIS SPECIES

FIELD OF THE INVENTION

This invention relates to increasing the expression of heterologous or chimeric proteins in plants, and more specifically to increasing protein expression in Arabidopsis species and other dicotyledons.

BACKGROUND OF THE INVENTION

One of the primary goals of plant genetic research and development is the production of transgenic plants that express a heterologous gene (i.e., produce a "foreign" protein) in an amount sufficient to confer a desired phenotype to the plant. While significant advances have been made in pursuit of this goal, the expression of certain heterologous genes in transgenic plants remains problematic. It is thought that numerous factors are involved in determining the ultimate level of expression of a heterologous gene in a plant. The amount of protein that is synthesized from a gene is a function of several complex and interrelated events, including transcription, RNA maturation, translation, and post-translational modification. Each of these processes is comprised of a large number of events, all of which are potentially regulated either independently or in concert.

The genetic code is considered "degenerate" in that more than one nucleic acid triplet (i.e., a "codon") encodes the same amino acid. Many amino acids may be coded for by several different codons. In general, genes within a taxonomic group exhibit similarities in codon choice, regardless of the function of these genes. Thus, an estimate of the overall use of the genetic ode by a taxonomic group can be obtained by summing codon frequencies of all its sequenced genes. Variation between degenerate base frequencies is not a neutral phenomenon, since systematic codon preferences have been reported for bacterial, yeast, plant and mammalian genes. Bias in codon choice within genes in a single species appears related to the level of expression of protein encoded by any particular gene.

Codon bias is most extreme in highly expressed proteins of bacteria (e.g., *E. coli*) and yeast. In unicellular organisms, highly expressed genes use a smaller subset of codons than do weakly expressed genes, although the codons preferred are distinct in some cases. Sharp and Li, *Nucl. Acids Res.* 14, 7734–7749 (1986), report that codon usage in 165 *E. coli* genes reveals a positive correlation between high expression and increased codon bias. In these organisms, a strong positive correlation has been reported between the abundance of an isoaccepting tRNA species and the favored synonymous codon. For example, in one group of highly expressed proteins in yeast, over 96% of the amino acids are encoded by only 25 of the 61 available codons. See Bennetzen and Hall, J. Biol. Chem. 257, 3026–3031. (1982). These 25 codons are preferred in all sequenced yeast genes, but the degree of preference varies with the level of expression of the genes. Biased codon choice in highly expressed genes appears to enhance translation, and is required for maintaining mRNA stability in yeast. It has been proposed that the good fit of abundant yeast and *E. coli* mRNA codon usage to isoacceptor tRNA abundance promotes high translation levels and high steady state levels of these proteins. These results strongly suggest that the potential for high levels of expression of plant genes in yeast or *E. coli* is limited by their codon usage, and conversely that high levels of expression of *E. Coli* or yeast genes in plant cells is similarly limited by the preferred codon usage of the different organisms.

Although plant codon usage patterns are distinct from those reported for bacteria, yeast, and animals, in general plant codon usage pattern more closely resembles that of higher eukaryotes than unicellular organisms, due to the overall preference for G+ C content in codon position III. Moreover, analysis of a large group of plant gene sequences indicates that synonymous codons are used differently by monocots and dicots. Wilbur et al., *Plant Physiol*. 92: 1–11 (1990), describes the difference in codon usage between bacteria and higher plants such as dicotyledonous and monocotyledonous plants. For example, the codon usages for codons XCG and XUA are 1.8% and 3.2% in dicotyledonous plants and 6.3% and 1.4% in monocotyledonous plants. The combined codon usage for codons XXC and XXG (hereinafter, referred to as the codon XXC/G usage, wherein each of the two Xs is independently selected from the group consisting of A, G, C and T) is 45% in dicotyledon and 73.5% in monocotyledon. It is well established that GC content in genes which can be translated is higher in monocotyledon such as gramineous plants, e.g., rice plants, than in dicotyledons. As to bacteria, the codon usage apparently varies by strain.

In this regard, investigators have determined that typical plant structural coding sequences preferentially utilize certain codons to encode certain amino acids in a different frequency than the frequency of usage appearing in bacterial or other non-plant coding sequences. Thus, it has been suggested that the differences between the typical codon usage present in plant coding sequences as compared to the typical codon usage present in non-plant coding sequence is a factor contributing to the low levels of non-plant mRNA and non-plant protein produced in transgenic plants. These differences in codon usage may contribute to the low levels of mRNA or protein expressed by the non-plant coding sequence in a transgenic plant by affecting the transcription or translation of the coding sequence or proper MRNA processing.

Recently, attempts have been made to alter the structural coding sequence of a desired polypeptide or protein in an effort to enhance its expression in the plant. In particular, investigators have altered the codon usage of heterologous, structural coding sequences (i.e., heterologous genes) in an attempt to enhance their expression in plants. Most notably, the sequence encoding insecticidal crystal proteins of *Bacillus thuringiensis* (Bt) has been modified in various ways to enhance its expression in a plant, particularly monocotyledonous plants, to produce commercially viable insect-tolerant plants.

U.S. Pat. No. 5,380,831 to Adang et al. describes synthetic Bt genes designed to be expressed at a level higher than naturally-occurring Bt genes. The genes utilize codons preferred in highly expressed monocot or dicot protein. Specifically, the synthetic genes, while about 85% homologous to the native bacterial sequence, are chemically modified to contain codons that are preferred by highly expressed plant genes, and to eliminate undesirable sequences that cause destabilization, termination of RNA, secondary structures and RNA splice sites.

U.S. Pat. No. 5,436,391 to Fujimoto et al. describes a synthetic gene encoding the insecticidal protein Bt. The gene is provided having a base sequence which has been modified to bring the codon usage in conformity with the genes of graminaceous plants, particularly rice plants (e.g., oryza).

U.S. Pat. No. 5,689,052 to Brown et al. describes a method for modifying a foreign nucleotide sequence for enhanced accumulation of its protein product in a monocotyledonous plant, and/or increasing the frequency of obtaining transgenic monocotyledonous plants which accumulate useful amounts of a transgenic protein, by reducing the frequency of the rare and semi-rare monocotyledonous codons in the foreign gene and replacing them with more preferred monocotyledonous codons.

Another approach to altering the codon usage of a Bt toxin gene to enhance its expression in plants is described in U.S. Pat. No. 5,500,365 to Fischhoff et al. Here, the synthetic plant gene was prepared by modifying the coding sequence to remove all ATTTA sequences and certain identified putative polyadenylation signals. Moreover, the gene sequence was scanned to identify regions with greater than four consecutive adenine or thymine nucleotides. If there were more than one of the minor polyadenylation signals identified within ten nucleotides of each other, then the nucleotide sequence of this region was altered to remove these signals while maintaining the original encoded amino acid sequence. The overall G+ C content was also adjusted to provide a final sequence having a G+ C ratio of about 50%. Similarly, U.S. Pat. No. 5,877,306 Cornelissen et al. discloses a method of modifying a DNA sequence encoding a Bt crystal protein toxin wherein the gene was modified by reducing the A+ T content. This was accomplished by changing the adenine and thymine bases to cytosine and guanine, while maintaining a coding sequence for the original protein toxin.

While the foregoing examples emphasize the modification or optimization of codon usage in heterologous structural genes (i.e., the genes encoding a desired protein product, such as Bt toxin), the modification of regulatory elements that control transcription by optimizing codon usage in the host plant has not been emphasized. It is widely recognized that the upstream regulatory elements that control transcription and translation have very significant roles in determining the quantity, timing, and tissue specificity of gene expression. Various nucleotide sequences other than the heterologous structural coding sequence affect the expression levels of a foreign DNA sequence introduced into a plant, including promoter sequences, intron sequences, 3' untranslated sequences, polyadenylation sites, and other regulatory sequences.

In view of the foregoing, activation and control of transcription are processes that may desirably be manipulated in order to achieve altered (i.e., increased or decreased) expression of a heterologous structural gene in a plant cell. Transcription can be activated through the use of two functional domains of a transcription activation moiety: a domain (i.e., sequence of amino acids) that recognizes and binds to a specific site or sequence of nucleotides on a target DNA, (the DNA binding domain); and a domain that is capable of activating transcription of the DNA when physically associated with the DNA-binding domain and which may be necessary for activation of the target gene (the activation domain). See Keegan, et al., *Science* 231, 669–704 (1986); Ma and Ptashne, *Cell* 48, 847–853 (1987). The two functional domains may be derived from a single transcription activation protein. Alternatively, it has been shown that these two functions can also reside on separate proteins. See McKnight et al., *Proc. Natl. Acad. Sci. USA* 89, 7061–7065 (1987); Curran et al. 55, 395–397 (1988). The transcription activation domains may also be derived from synthetic DNA-binding and transcription activation proteins.

Additional flexibility in controlling heterologous gene expression in plants may be obtained by using DNA binding domains and response elements from heterologous sources (i.e., DNA binding domains from non-plant sources). Some examples of such heterologous DNA binding domains include the LexA and GAL4 DNA binding domains. The LexA DNA-binding domain is part of the repressor protein LexA from *Escherichia coli* (*E. Coli*) (Brent and Ptashne, *Cell* 43:729–736 (1985)).

Although the LexA DNA binding domain functions as an efficient DNA binding domain in its natural bacterial host, when transferred by recombinant DNA technology into higher eukaryotes such as plants, the domain is not efficiently expressed. Accordingly, it would be desirable to alter the LexA DNA binding domain to increase its expression in higher eukaryotes such as plants.

SUMMARY OF THE INVENTION

Certain objects, advantages and novel features of the invention will be set forth in the description that follows, and will become apparent to those skilled in the art upon examination of the following, or may be learned with the practice of the invention.

It is an object of the invention to provide a synthetic LexA DNA binding domain optimized for codon usage in plants, more specifically in dicots, and most specifically in *Arabidopsis thaliana.*

The invention relates to adapting the codons of the DNA binding domain of the LexA gene from *E. Coli* to the codon usage of *Arabidopsis thaliana*. This method is advantageous in that it allows for the increased expression of heterologous and chimeric proteins containing this artificial DNA binding domain.

Additional aspects of this invention include constructs (i.e., vectors, DNA fusions and polynucleotides), comprising the synthetic DNA sequence of the present invention. These constructs are useful for increasing heterologous protein expression in plant cells. Further aspects of the invention are cells, plant lines, and transgenic plants transformed with the described constructs. Methods of increasing expression of heterologous proteins in a cell or a transgenic plant are an additional aspect of the present invention.

The foregoing and other aspects of the present invention are explained in detail in the specification set forth below.

BRIEF DESCRIPTION OF THE DRAWINGS

FIG. 1 sets forth the nucleotide and amino acid sequences of the LexA DNA binding domain optimized for *Arabidopsis thaliana* codon usage.

FIG. 2 sets forth the nucleotide sequences of the seven oligonucleotides (SEQ ID NO: 3–9) that were annealed together to arrive at the LexA DNA binding domain optimized for *Arabidopsis thaliana* codon usage. SEQ ID NO: 10 is the LexA activation domain to which the LexA binding domain normally binds.

FIG. 3 is a schematic representation of the plasmid pUCNLSTBP1.

DETAILED DESCRIPTION OF THE PREFERRED EMBODIMENTS

The present invention will now be described more fully hereinafter with reference to the accompanying figures, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., *Patent In User Manual*, 99–102 (Nov. 1990) (U.S. Patent and Trademark Office).

The term "amino acid sequence," as used herein, refers to either a naturally occurring or a synthetic oligopeptide, peptide, polypeptide, or protein sequence, and fragments thereof. Where "amino acid sequence" is recited herein to refer to an amino acid sequence of a naturally occurring protein molecule, the term "amino acid sequence," and like terms, are not meant to limit the amino acid sequence to the complete, native amino acid sequence associated with the recited protein molecule.

The term "nucleic acid sequence" as used herein refers to a nucleotide, oligonucleotide, or polynucleotide, and fragments thereof, and to DNA or RNA of genomic or synthetic origin which may be single- or double-stranded, and which may represent a sense or antisense strand.

"Chemically synthesized," as related to a sequence of DNA, means that the component nucleotides are assembled in vitro. Manual chemical synthesis of DNA may be accomplished using well established procedures (Caruthers, M., in *Methodology of DNA and RNA Sequencing*, Chapter 1 (Weissman (ed.), Praeger Publishers, New York, (1983)). Alternatively, automated chemical synthesis of DNA can be performed using one of a number of commercially available apparatus.

As used herein, the term "LexA" or "LexA binding domain" refers to a protein or domain that is naturally encoded in *E. coli* by the lexA gene, which domain normally binds to the DNA sequence CATACTGTATGAGCATACAG (the LexA activation domain) [SEQ ID NO:10]. The term "LexA binding domain adapted (or optimized) for *Arabidopsis thaliana* usage" means a protein domain in which the codons encoding the domain have been modified from the natural *E. Coli* sequence in order to maximize DNA binding (and accordingly, transcription) in *Arabidopsis thaliana*.

As used herein, the term "expression" refers to the transcription and translation of a heterologous or homologous gene to yield the protein encoded by the gene.

"Heterologous" is used to indicate that a nucleic acid sequence (e.g., a gene) or a protein has a different natural origin or source with respect to its current host. "Heterologous" is also used to indicate that one or more of the domains present in a protein differ in their natural origin with respect to other domains present.

As used herein, a "structural gene" is that portion of a gene comprising a DNA segment encoding a protein, polypeptide or a portion thereof, and excluding the 5' sequence which drives the initiation of transcription. The structural gene may be one which is normally found in the cell or one which is not normally found in the cellular location wherein it is introduced, in which case it is termed a heterologous gene. A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be a composite of segments derived from a plurality of sources, either naturally occurring or synthetic, or both. When synthesizing a gene for improved expression in a host cell it is desirable to design the gene such that its frequency of codon usage approaches the frequency of preferred codon usage of the host cell.

As used herein, the term "chimeric protein" is used to indicate that the protein is comprised of domains, at least one of which has an origin or source that is heterologous with respect to the other domains present. Chimeric proteins are encoded by nucleotide sequences that have been fused or ligated together, resulting in a coding sequence that does not occur naturally. "Chimeric sequences" or genes refer to nucleic acid sequences containing at least two heterologous parts, e.g., parts derived from naturally occurring nucleic acid sequences that are not associated in their naturally occurring states, or containing at least one part that is of synthetic origin and not found in nature.

To improve expression of the DNA-binding domain of the LexA repressor protein in plants, the codon usage of the natural, *E. Coli* LexA DNA binding domain was modified and optimized to the codon usage of *Arabidopsis thaliana*. The characteristics of codon usage for *Arabidopsis thaliana* is based on the report of Wada et al., "Codon Usage Tabulated From The GenBank Genetic Sequence Data," *Nucleic Acids Research* 19 (Supp.) 1981–1986 (1991). Table 1, below, based upon the data provided in the Wada et al. article, illustrates the differences between the codons preferred by *E. Coli* for each amino acid vs. the codons preferred by *A. thaliana* for each amino acid (the codon listed in the table being the most preferred codon, according to the Wada et al. data).

In order to construct a synthetic DNA sequence in accordance with the present invention, the amino acid sequence of the *E. Coli* LexA DNA binding domain is determined and back-translated into all the available codon choices for each amino acid. The amino acid sequence of the protein can be analyzed using commercially available computer software such as the BACKTRANSLATE® program of the GCG Sequence Analysis software package. After the sequence is back-translated, the codons that are preferentially and optimally used in *Arabidopsis thaliana* are substituted for the naturally occurring codons of the *E Coli*. LexA binding domain. In other words, for each amino acid of the LexA DNA binding domain that may be encoded for by more than one codon, the codon preferred by *Arabidopsis thaliana* is placed in the sequence in place of the original codon. The result of the back-translation of the LexA DNA binding protein into codons that are preferred by *Arabidopsis thaliana*, when all codons of the *E. Coli* LexA binding domain are replaced with the preferred codons of *A. thaliana*, results in a DNA sequence of 258 nucleotides that encodes the LexA DNA binding domain optimized for use in *Arabidopsis thaliana*.

TABLE 1

Preferred Codon Usage of *E. Coli* vs. *A. thaliana*. Data taken from Wada et al., "Codon Usage Tabulated From The GenBank Genetic Sequence Data," Nucleic Acids Research 19 (Supp.) 1981–1986(1991)

| Amino Acid | Preferred Codon For *E. Coli* | Preferred Codon for *A. thaliana* |
|---|---|---|
| ARG | CGT | AGA |
| LEU | CTG | CTT |
| SER | AGC | TCT |
| THR | ACC | ACC |
| PRO | CCG | CCA |
| ALA | GCG | GCT |
| GLY | GGC | GGA |
| VAL | GTT | GTT |
| LYS | AAA | AAG |
| ASN | AAC | AAC |
| GLN | CAG | CAG |
| HIS | CAT | CAC |
| GLU | GAA | GAG |
| ASP | GAT | GAT |
| TYR | TAT | TAC |
| CYS | TGC | TGC |
| PHE | TTT | TTC |
| ILE | ATC | ATC |
| MET | ATG | ATG |
| TRP | TGG | TGG |

As further explained herein in the Examples, and in one preferred embodiment of the invention, after the DNA sequence encoding the LexA DNA binding domain completely optimized for use in *Arabidopsis thaliana* is determined, the 258 nucleotides representing one strand of the DNA is arbitrarily divided into three oligonucleotide sequences. The 258 nucleotides representing the other, complementary strand of the DNA is arbitrarily divided into four oligonucleotide sequences. The oligonucleotide sequences are then chemically synthesized into seven oligomers, each being phosphorylated at their 5' end. In addition, four of the oligomers have additional nucleotides added to the ends in order to create "sticky ends" (restriction sites) for use in ligating the DNA into recombinant vectors. After the seven oligomers are synthesized, the oligomers are annealed together, to yield the following synthetic DNA sequence encoding the LexA DNA binding domain codon optimized for usage in *Arabidopsis thaliana*:

ATGAAGGCTCTTACCGCTAGACAGCAG-
GAGGTTTTCGATCTTATCAGAGATCACATCT
CTCAGACCGGAATGCCACCAACCA-
GAGCTGAGATCGCTCAGAGACTTGGAT-
TCAGAT CTCCAAACGCTGCTGAGGAGCACCT-
TAAGGCTCTTGCTAGAAAGGGAGTTATCGAGA
TCGTTTCTGGAGCTTCTAGAGGAATCA-
GACTTCTTCAGGAGGAGGAGGGACTTC
CACTTGTTGGMGAGTTGCTGCTGGAGAG (SEQ ID NO:1, also set forth in FIG. 1)

which DNA sequence translates into the following amino acid sequence of the LexA DNA binding domain codon optimized for *Arabidopsis thaliana*:

Met-Lys-Ala-Leu-Thr-Ala-Arg-Gln-Gln-Glu-Val-Phe-
Asp-Leu-Ile-Arg-Asp-His-Ile-Ser-Gln-Thr-Gly-Met-
Pro-Pro-Thr-Arg-Ala-Glu-Ile-Ala-Gln-Arg-Leu-Gly-
Phe-Arg-Ser-Pro-Asn-Ala-Ala-Glu-Glu-His-Leu-Lys-
Ala-Leu-Ala-Arg-Lys-Gly-Val-Ile-Glu-Ile-Val-Ser-
Gly-Ala-Ser-Arg-Gly-Ile-Arg-Leu-Leu-Gln-Glu-Glu-
Glu-Glu-Gly-Leu-Pro-Leu-Va-IGly-Arg-Val-Ala-Ala-
Gly-Glu (SEQ ID NO:2, also set forth in FIG. 1).

The foregoing description describes a particularly preferred embodiment of the invention in which every codon encoding the normal, *E. Coli* LexA DNA binding domain is substituted with a corresponding codon that is preferred by *A. thaliana* (i.e., is completely or 100 percent optimized for usage by *A. thaliana*), when the two codons are different (i.e., when a particular amino acid may be encoded by more than one codon, and a codon preferred by *E. Coli* differs from one preferred by *A. thaliana*). The invention also encompasses synthetic nucleotide sequences and proteins that are partially (i.e., less than 100 percent) optimized for usage by *A. thaliana*, and the uses therefor. In this alternative embodiment of the invention, using the methods described above, less than all of amino acids of the LexA DNA binding domain that may be encoded for by more than one codon is replaced in the synthetic sequence with a codon preferred by *A. thaliana*. Preferably, more than about 50 percent of the codons of the LexA binding domain are replaced in the synthetic sequence with a codon preferred by *A. thaliana*; more preferably, more than about 80 percent of the codons of the LexA binding domain are replaced in the synthetic sequence with a codon preferred by *A. thaliana*; most preferably, 100 percent of the codons of the LexA binding domain are codons that are preferred by *A. thaliana*.

The synthetic nucleotide sequences and proteins set forth in the present invention are described as being optimized for usage in Arabidopsis species, particularly *Arabidopsis thaliana*; however, the skilled artisan will appreciate that the synthetic nucleotide sequences and proteins encoding the Lex A DNA binding domain optimized for Arabidopsis usage are useful in non-bacterial species other than *Arabidopsis thaliana*. The LexA DNA binding domain set forth herein will be more efficiently expressed in higher eukaryotes (e.g., plants and animals), and more specifically will be more efficiently expressed in dicotyledenous plants, which include but are by no means limited to species of legumes (from the family Fabaceae), including soybean, peanut, and alfalfa; species of the Solanaceae family such as tomato, eggplant and potato; species of the family Brassicaceae such as cabbage, turnips and rapeseed; species of the family Rosaceae such as apples, pears and berries; and members of the families Cucurbitaceae (cucumbers), Chenopodiaceae (beets) and Umbelliferae (carrots).

The present invention provides an advantageously modified DNA binding domain for the enhanced expression of desired heterologous protein genes in transgenic plants. To this end, one embodiment of the present invention is a DNA construct comprising a DNA sequence encoding the LexA synthetic DNA binding domain of the invention. Such DNA constructs accordingly provide for the preparation of stably transformed cells expressing heterologous protein, which transformed cells are also an aspect of the invention. Still further, the synthetic DNA binding domain of the present invention provides for the subsequent regeneration of fertile, transgenic plants and progeny containing desired heterologous protein genes. These aspects of the invention are further described herein below.

DNA constructs (also referred to herein as DNA vectors) of the present invention comprise the nucleotide sequence of the synthetic Lex A binding domain described herein, which nucleotide sequence is preferably the sequence provided herein as SEQ ID NO:1. The preparation of DNA constructs is well known in the art. See, e.g., Sambrook et al., *Molecular Cloning: A Laboratory Manual* (1989). The DNA constructs of the present invention are useful in the transformation of cells (e.g., plant cells), and thus useful in the expression of heterologous genes in the cells. The expression of a heterologous DNA sequence (i.e., gene) in a plant requires proper transcriptional initiation regulatory regions that are recognized in the host plant to be transformed, with the regions linked in a manner which permits the transcription of the coding sequence and subsequent processing in the nucleus. Thus, a DNA construct preferably contains some or all of the necessary elements to permit the transcription and ultimate expression of the coding sequence in the host plant.

DNA constructs of the present invention may contain suitable promoters for the expression of heterologous genes in plants. The term "promoter" refers to the nucleotide sequences at the 5' end of a structural gene which direct the initiation of transcription. Generally, promoter sequences are necessary, but not always sufficient, to drive the expression of a downstream gene. In the construction of heterologous promoter/structural gene combinations, the structural gene is placed under the regulatory control of a promoter such that the expression of the gene is controlled by promoter sequences. The promoter is positioned preferentially upstream to the structural gene and at a distance from the transcription start site that approximates the distance between the promoter and the gene it controls in its natural setting. As is known in the art, some variation in this distance can be tolerated without loss of promoter function. As used herein, the term "operatively linked" means that a promoter is connected to a coding region in such a way that the transcription of that coding region is controlled and regulated by that promoter. Means for operatively linking a promoter to a coding region are well known in the art.

For expression in plants, suitable promoters must be chosen for the host cell, the selection of which promoters is well within the skill of one knowledgeable in the art. Promoters useful in the practice of the present invention include, but are not limited to, constitutive, inducible, temporally regulated, developmentally regulated, chemically regulated, tissue-preferred and tissue-specific promoters.

Numerous promoters are known or are found to facilitate transcription of RNA in plant cells and can be used in the DNA construct of the present invention. Examples of suitable promoters include the nopaline synthase (NOS) and octopine synthase (OCS) promoters, the light-inducible promoter from the small subunit of ribulose bis-phosphate carboxylase promoters, the CaMV 35S and 19S promoters, the full-length transcript promoter from Figwort mosaic virus, histone promoters, tubulin promoters, or the mannopine synthase promoter (MAS). The promoter may also be one that causes preferential expression in a particular tissue, such as leaves, stems, roots, or meristematic tissue, or the promoter may be inducible, such as by light, heat stress, water stress or chemical application or production by the plant. Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters.

Additional promoters useful in the present invention include but are not limited to one of several of the actin genes, which are known to be expressed in most cell types. Yet another constitutive promoter useful in the practice of the present invention is derived from ubiquitin, which is another gene product known to accumulate in many cell types. The ubiquitin promoter has been cloned from several species for use in transgenic plants (e.g., sunflower (Binet et al., *Plant Science* 79: 87–94 (1991); and maize (Christensen et al., *Plant Molec. Biol.* 12, 619–632 (1989)). Further useful promoters are the U2 and U5 snRNA promoters from maize (Brown et al., *Nucleic Acids Res.* 17, 8991 (1989)) and the promoter from alcohol dehydrogenase (Dennis et al., *Nucleic Acids Res.* 12, 3983 (1984)).

Tissue-specific or tissue-preferential promoters useful in the present invention in plants are those which direct expression in root, pith, leaf or pollen. Such promoters are disclosed in U.S. Pat. No. 5,625,136 (herein incorporated by reference in its entirety). Also useful are promoters which confer seed-specific expression, such as those disclosed by Schermthaner et al., *EMBO J.* 7: 1249 (1988); anther-specific promoters ant32 and ant43D; anther (tapetal) specific promoter B6 (Huffman et al., *J. Cell. Biochem.* 17B, Abstract #D209 (1993)); and pistil-specific promoters such as a modified S13 promoter (Dzelkalns et al., *Plant Cell* 5,855 (1993)).

Other plant promoters may be obtained, preferably from plants or plant viruses, and may be utilized so long as the selected promoter is capable of causing sufficient expression in a plant resulting in the production of an effective amount of the desired protein. Preferred constitutive promoters include but are not limited to the CaMV 35S and 19S promoters (see U.S. Pat. No. 5,352,605, the disclosure of which is incorporated herein in its entirety). Any promoter used in the present invention may be modified, if desired, to alter their control characteristics. For example, the CaMV 35S or 19S promoters may be enhanced by the method described in Kay, et al. *Science* (1987) Vol. 236, pp.1299–1302.

The DNA sequences that comprise the DNA constructs of the present invention are preferably carried on suitable vectors, which are known in the art. Preferred vectors for are plasmids that may be propagated in a plant cell. Particularly preferred vectors for transformation are those useful for transformation of plant cells or of Agrobacteria, as described further below. For Agrobacterium-mediated transformation, the preferred vector is a Ti-plasmid derived vector. Other appropriate vectors which can be utilized as starting materials are known in the art. Suitable vectors for transforming plant tissue and protoplasts have been described by deFramond, A. et al., *Bio/Technology* 1, 263 (1983); An, G. et al., *EMBO J.* 4, 277 (1985); and Rothstein, S. J. et al., *Gene* 53, 153 (1987). In addition to these, many other vectors have been described in the art which are suitable for use as starting materials in the present invention.

The DNA encoding the synthetic LexA binding domain of the present invention, and the DNA constructs comprising them, have applicability to any structural gene that is desired to be introduced into a plant to provide any desired characteristic in the plant, such as herbicide tolerance, virus tolerance, insect tolerance, disease tolerance, drought tolerance, or enhanced or improved phenotypic characteristics such as improved nutritional or processing characteristics.

In a particularly preferred embodiment of the invention, DNA constructs of the present invention also comprise DNA sequences encoding transactivation domains. Transactivation domains can be defined as amino acid sequences that, when combined with the DNA binding domain, increase productive transcription initiation by RNA polymerases. (See generally Ptashne, *Nature* 335, 683–689 (1988)). Different transactivation domains are known to have different degrees of effectiveness in their ability to increase transcription initiation. In the present invention it is desirable to use transactivation domains that have superior transactivating effectiveness in plant cells in order to create a high level of target polypeptide expression in response to the presence of chemical ligand.

Transactivation domains that have been shown to be particularly effective in the method of the present invention include but are not limited to VP16 (isolated from the herpes simplex virus), C1 (isolated from maize), and Thm18 (isolated from tomato). One preferred example for the use of codon-optimized LexA DNA-binding domain is the in-frame fusion of this DNA-binding domain to other domains that have other functions; for example, the fusion to transcription activator domains like VP16 from *Herpes simplex* or Thm18 from tomato, or the fusion to TATA-box binding proteins (TBPs) such as the TBP1 protein from *Arabidopsis thaliana*. Other transactivation domains may also be effective.

Transgenes (heterologous genes to be transformed into a plant cell) will often be genes that direct the expression of a particular protein or polypeptide product, but they may also be non-expressible DNA segments, e.g., transposons that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

Any heterologous gene or nucleic acid that is desired to be expressed in a plant is suitable for the practice of the present invention. Heterologous genes to be transformed and expressed in the plants of the present invention include but are not limited to genes that encode resistance to diseases and insects, genes conferring nutritional value, genes conferring antifungal, antibacterial or antiviral activity, and the like. Alternatively, therapeutic (e.g., for veterinary or medical uses) or immunogenic (e.g., for vaccination) peptides and proteins can be expressed in plants transformed with the synthetic DNA LexA DNA binding domain of the present invention. Likewise, the transfer of any nucleic acid for controlling gene expression in a plant is contemplated as an aspect of the present invention. For example, the nucleic acid to be transferred can encode an antisense oligonucleotide. Alternately, plants may be transformed with one or more genes to reproduce enzymatic pathways for chemical synthesis or other industrial processes.

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transform cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention. The selectable marker gene may be the only heterologous gene expressed by a transformed cell, or may be expressed in addition to another heterologous gene transformed into and expressed in the transformed cell. Selectable marker genes are utilized for the identification and selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al., *EMBO J.* 6, 2513 (1987); DeBlock et al., *Plant Physiol.* 91, 691 (1989); Fromm et al., *BioTechnology* 8, 833 (1990); Gordon-Kamm et al., Plant *Cell* 2, 603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

Selectable marker genes include, but are not limited to, genes encoding: neomycin phosphotransferase II (Fraley et al., *CRC Critical Reviews in Plant Science* 4, 1 (1986)); cyanamide hydratase (Maier-Greiner et al., *Proc. Natl. Acad. Sci. USA* 88, 4250 (1991)); aspartate kinase; dihydrodipicolinate synthase (Perl et al., *BioTechnology* 11, 715 (1993)); bar gene (Toki et al., *Plant Physiol.* 100, 1503 (1992); Meagher et al., *Crop Sci.* 36, 1367 (1996)); tryptophane decarboxylase (Goddijn et al., *Plant Mol. Biol.* 22, 907 (1993)); neomycin phosphotransferase (NEO; Southern et al., *J. Mol. Appl. Gen.* 1, 327 (1982)); hygromycin phosphotransferase (HPT or HYG; Shimizu et al., *Mol. Cell. Biol.* 6, 1074 (1986)); dihydrofolate reductase (DHFR); phosphinothricin acetyltransferase (DeBlock et al., *EMBO J.* 6, 2513 (1987)); 2,2- dichloropropionic acid dehalogenase (Buchanan-Wollatron et al., *J. Cell. Biochem.* 13D, 330 (1989)); acetohydroxyacid synthase (U.S. Pat. No. 4,761, 373 to Anderson et al.; Haughn et al., *Mol. Gen. Genet.* 221, 266 (1988)); 5-enolpyruvyl-shikimate-phosphate synthase (aroA; Comai et al., *Nature* 317, 741 (1985)); haloarylnitrilase (WO 87/04181 to Stalker et al.); acetyl-coenzyme A carboxylase (Parker et al., *Plant Physiol.* 92, 1220 (1990)); dihydropteroate synthase (sulI; Guerineau et al., *Plant Mol. Biol.* 15, 127 (1990)); and 32 kDa photosystem II polypeptide (psbA; Hirschberg et al., *Science* 222, 1346 (1983)).

Also included are genes encoding resistance to: chloramphenicol (Herrera-Estrella et al., *EMBO J.* 2, 987 (1983)); methotrexate (Herrera-Estrella et al., *Nature* 303, 209 (1983); Meijer et al., *Plant Mol. Biol.* 16, 807 (1991)); hygromycin (Waldron et al., *Plant Mol. Biol.* 5, 103 (1985); Zhijian et al., *Plant Science* 108, 219 (1995); Meijer et al., *Plant Mol. Bio.* 16, 807 (1991)); streptomycin (Jones et al., *Mol. Gen. Genet.* 210, 86 (1987)); spectinomycin (Bretagne-Sagnard et al., *Transgenic Res.* 5, 131 (1996)); bleomycin (Hille et al., *Plant Mol. Biol.* 7, 171 (1986)); sulfonamide (Guerineau et al., *Plant Mol. Bio.* 15, 127 (1990); bromoxynil (Stalker et al., *Science* 242, 419 (1988)); 2,4-D (Streber et al., *Bio/Technology* 7, 811 (1989)); phosphinothricin (DeBlock et al., *EMBO J.* 6, 2513 (1987)); spectinomycin (Bretagne-Sagnard and Chupeau, *Transgenic Research* 5, 131 (1996)).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See generally, Yarranton, *Curr. Opin. Biotech.* 3, 506 (1992); Chistopherson et al., *Proc. Natl. Acad. Sci. USA* 89, 6314 (1992); Yao et al., *Cell* 71, 63 (1992); Reznikoff, *Mol. Microbiol.* 6, 2419 (1992); Barkley, et al., *The Operon* 177–220 (1980); Hu et al., *Cell* 48, 555 (1987); Brown et al., *Cell* 49, 603 (1987); Figge et al., *Cell* 52, 713 (1988); Deuschle et al., *Proc. Natl. Acad. Sci. USA* 86, 5400 (1989); Fuerst et al., *Proc. Natl. Acad. Sci. USA* 86, 2549 (1989); Deuschle et al., *Science* 248, 480 (1990); Labow et al., *Mol Cell. Biol.* 10, 3343 (1990); Zambretti et al., *Proc. Natl. Acad. Sci. USA* 89, 3952 (1992); Baim et al., *Proc. Natl. Acad. Sci. USA* 88, 5072 (1991); Wyborski et al., *Nuc. Acids Res.* 19, 4647 (1991); Hillenand-Wissman, *Topics in Mol. And Struc. Biol.* 10, 143 (1989); Degenkolb et al., *Antimicrob. Agents Chemother.* 35, 1591 (1991); Kleinschnidt et al., *Biochemistry* 27, 1094 (1988); Gatz et al., *Plant J.* 2, 397 (1992); Gossen et al., *Proc. Natl. Acad. Sci. USA* 89, 5547 (1992); Oliva et al., *Antimicrob. Agents Chemother.* 36, 913 (1992); Hlavka et al., Handbook of Experimental Pharmacology 78, (1985); and Gill et al., *Nature* 334, 721 (1988). The disclosures described herein are incorporated by reference.

The above list of selectable marker genes are not meant to be limiting. Any selectable marker gene can be used in the present invention.

In view of the foregoing, it is apparent that one aspect of the present invention are transformed plant cells comprising the synthetic LexA DNA binding domain of the present invention. "Transformation", as defined herein, describes a process by which heterologous nucleic acid enters and changes a recipient cell. It may occur under natural or artificial conditions using various methods well known in the art. Transformation may rely on any known method for the insertion of foreign nucleic acid sequences into a eukaryotic host cell. Such "transformed" cells include stably transformed cells in which the inserted DNA is capable of replication either as an autonomously replicating plasmid or as part of the host chromosome. They also include cells which transiently express the inserted DNA or RNA for limited periods of time.

In a preferred embodiment of the invention, recipient cells for transformation are plant cells, more preferably dicot plant cells, even more preferably Arabidopsis species plant cells, and most preferably *Arabidopsis thaliana* plant cells. "Plant cells" as used herein includes plant cells in plant tissue or plant tissue and plant cells and protoplasts in culture. Plant tissue includes differentiated and undifferentiated tissues of plants, including but not limited to, roots, shoots, leaves, pollen, seeds, tumor tissue and various forms of cells in culture, such as single cells, protoplasts, embryos and callus tissue. The plant tissue may be in plant, or in organ, tissue or cell culture.

The recombinant DNA molecule carrying the synthetic LexA DNA binding domain of the invention and optionally a structural gene under promoter control can be introduced into plant tissue by any means known to those skilled in the art. The technique used for a given plant species or specific type of plant tissue depends on the known successful techniques. As novel means are developed for the stable insertion of foreign genes into plant cells and for manipulating the modified cells, skilled artisans will be able to select from known means to achieve a desired result. Means for introducing recombinant DNA into plant tissue include, but are not limited to, direct DNA uptake (Paszkowski, J. et al. (1984) *EMBO J.* 3,2717), electroporation (Fromm, M., et al. *Proc. Natl. Acad. Sci. USA* 82,5824 (1985), microinjection (Crossway, A. et al. *Mol. Gen. Genet.* 202, 179 (1986)), or T-DNA mediated transfer from Agrobacterium tumefaciens to the plant tissue, which techniques are known in the art. There appears to be no fundamental limitation of T-DNA transformation to the natural host range of Agrobacterium. Representative T-DNA vector systems are described in the following references: An, G. et al. *EMBO J.* 4, 277 (1985); Herrera-Estrella, L. et al., *Nature* 303, 209 (1983); Herrera-Estrella, L. et al. *EMBO J.* 2, 987 (1983); Herrera-Estrella, L. et al. in *Plant Genetic Engineering*, New York: Cambridge University Press, p. 63 (1985). Once introduced into the plant tissue, the expression of the structural gene may be assayed by any means known to the art, and expression may be measured as mRNA transcribed or as protein synthesized, as provided herein.

Transgenic plants comprising the synthetic LexA DNA binding domain of the present invention (as present, for example, in a DNA construct of the present invention, or a transformed cells of the present invention) are also an aspect of the present invention. Procedures for cultivating transformed cells to useful cultivars are known to those skilled in the art. Techniques are known for the in vitro culture of plant tissue, and in a number of cases, for regeneration into whole plants. A further aspect of the invention are plant tissue, plants or seeds containing the chimeric DNA sequences described above. Preferred are plant tissues, plants or seeds containing those chimeric DNA sequences which are mentioned as being preferred.

The invention thus relates, in certain embodiments, to transgenic plants comprising the synthetic LexA DNA binding domain of the present invention. As used herein, the term "transgenic plants" is intended to refer to plants that have incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. It is contemplated that in some instances the genome of transgenic plants of the present invention will have been augmented through the stable introduction of the transgene. However, in other instances, the introduced gene will replace an endogenous sequence.

One example of a transgenic plant of the present invention may be prepared by the process of creating a translational fusion protein gene and introducing the fusion into a plant. One example of a plant to be transformed by the methods of the invention is a wild-type Arabidopsis. A specific illustration of the method of the invention would involve constructing gene fusions comprising the LexA DNA binding domain optimized for usage in *Arabidopsis thaliana* and a DNA segment encoding an exogenous protein one desires to express, and introducing the fusion into wild-type Arabidopsis.

Alternatively, the gene introduced into the transformed plant line will comprise an exogenous protein gene operatively linked to its own promoter or another promoter that is active in plants. This gene will contain the cloned LexA DNA binding domain optimized for *Arabidposis thaliana* in a DNA construct for the purpose of increasing the expression of that exogenous protein gene.

The transformed cells, identified by selection or screening and cultured in an appropriate medium that supports regeneration as provided herein, will then be allowed to mature into plants. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. After the regenerating plants have reached the stage of shoot and root development, they may be transferred to a greenhouse for further growth and testing. Progeny may be recovered from the transformed plants and tested for expression of the exogenous expressible gene by localized application of an appropriate substrate to plant parts such as leaves.

The regenerated plants are screened for transformation by standard methods illustrated below. Progeny of the regenerated plants is continuously screened and selected for the continued presence of the integrated DNA sequence in order to develop improved plant and seed lines. The DNA sequence can be moved into other genetic lines by a variety of techniques, including classical breeding, protoplast fusion, nuclear transfer and chromosome transfer.

After effecting delivery of heterologous DNA to recipient cells and plants by any of the methods discussed above, identifying the cells exhibiting successful or enhanced expression of a heterologous gene for further culturing and plant regeneration generally occurs. As mentioned above, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene.

"Screening" generally refers to identifying the cells exhibiting expression of a heterologous gene that has been transformed into the plant. Usually, screening is carried out to select successfully transformed seeds (i.e., transgenic seeds) for further cultivation and plant generation (i.e., for the production of transgenic plants). As mentioned above, in order to improve the ability to identify transformants, one may desire to employ a selectable or screenable marker gene as, or in addition to, the heterologous gene of interest. In this case, one would then generally assay the potentially transformed cells, seeds or plants by exposing the cells, seeds, plants, or seedlings to a selective agent or agents, or one would screen the cells, seeds, plants or tissues of the plants for the desired marker gene. For example, transgenic cells, seeds or plants may be screened under selective conditions, such as by growing the seeds or seedlings on media containing selective agents, such as antibiotics (e.g., hygromycin, kanamycin, paromomycin or BASTA®), the successfully transformed plants having been transformed with genes encoding resistance to such selective agents.

To additionally confirm the presence of the heterologous nucleic acid or "transgene(s)" in the seeds of the cultivated plant or the in the regenerated plants produced from those seeds, a variety of assays may be performed. Such assays include, for example, molecular biological assays, such as Southern and Northern blotting and PCR; biochemical assays, such as detecting the presence of a protein product, e.g., by immunological means (ELISAs and Western blots) or by enzymatic function; by plant part assays, such as leaf or root assays; and also, by analyzing the phenotype of the whole regenerated plant.

While Southern blotting and PCR may be used to detect the gene(s) in question, they do not provide information as to whether the gene is being expressed. Expression of the heterologous gene may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these techniques are among the most commonly employed, other procedures are known in the art and may be additionally used.

The following Examples are provided to illustrate the present invention, and should not be construed as limiting thereof.

EXAMPLE 1

Production of the LexA DNA Binding Domain Adapted for Usage in Arabidopsis

The 86-amino acid residues of the *E. Coli* DNA-binding domain of LexA were translated back to a sequence of nucleic acids, substituting the *E. Coli* codon with the codons that are most frequently utilized in *Arabidopsis thaliana*, according to K. Wada, et al., *Nucleic Acids Res.* 19, 1981–1986 (1991).

The result of the translation back was a DNA sequence of 258 nucleic acid residues. The sequence representing one strand of a double-stranded DNA encoding the LexA DNA binding domain was divided into three segments of 84, 90 and 84 nucleotides, respectively. The DNA sequence of 258 nucleic acid residues representing the other (i.e., complementary) strand of the double-stranded DNA encoding the LexA DNA binding domain was divided into four segments of 51, 81, 81 and 45 nucleic acid residues.

The DNA sequences of the three segments of the first strand were as follows:

A G C T T C A T A T G A A G G C T C T T A C C G C T A- GACAGCAGGAGGTTTTCGATCTTATC AGAGAT- C A C A T C T C T C A G A C G G G A A T G C C A C- CAACCAGA [SEQ ID NO: 3]

G C T G A G A T C G C T C A G A G A C T T G G A T T C A- GATCTCCAAACGCTGCTGAGGAGC ACCT- TAAGGCTCTTGCTAGAAAGGGAGTTATC- GAGATC [SEQ ID NO:4]

G T T T C T G G A G C T T C T A G A G G A A T C A- GACTTCTTCAGGAGGAGGAGGAGGGA CTTC- CACTTGTTGGAAGAGTTGCTGCTGGAGAGG [SEQ ID NO:5]

The DNA sequences of the four segments of the second strand were as follows:

A T C T C T G A T A A G A T C G A A A A C C T C C T- GCTGTCTAGCGGTAAGAGCCTTCATAT GA [SEQ ID NO:6]

CTCAGCAGCGTTTGGAGATCTGAATC-
CAAGTCTCTGAGCGATCTCAGCTCTG GTTG-
GTGGCATTCCGGTCTGAGAGATGTG [SEQ ID
NO:7]
CTCCTGTGAAGAAGTCGGATTCCTCTA-
GAAGCTCCAGAAACGATGCTCGATACTC
CCTTTCTAGGCAAGAGCCTTAAGGTGCTC [SEQ
ID NO:8]
GATCCGCTCTCCAGAGCAACTCTTCCAA-
CAAGTGGAAGTCCGTCCTCCTC [SEQ ID NO:9]

The seven sequences described above were chemically synthesized as DNA oligomers on a modified ABI 391 machine, using standard β-cyano-ethyl chemistry, each oligomer being phosphorylated at their 5' ends. Four of the oligomers also had additional nucleotides added to their ends to create restrictions sites ("sticky ends") for the purpose of ligating an annealed DNA product into a cloning vector at has been digested with the restriction enzymes HindIII and BamHI.

The seven oligomers were then annealed together. For annealing of the seven oligomers with each other, the desiccated oligomers were dissolved at high concentration (10 OD$_{260}$ units/100 µl) in STE buffer (50 mM NaCl, 10 mM Tris pH 8.0, 1 mM EDTA). Equal volumes (12 µl each) were mixed in a 1.5 ml centrifuge tube and heated in a water bath to 94° C., then slowly cooled down to room temperature over about 3 hours by "unplugging" the water bath (i.e., by allowing the water bath to reach room temperature naturally). The DNA was precipitated by adding 0.5 volumes (42 µl) of 7.5 M ammonium acetate and 0.03 volumes of 1M MgCl$_2$ and 2.5 volumes of ethanol with mixing, followed by incubation at 4° C. for 12 hours, and centrifugation for 15 minutes at room temperature (RT) at 14,000 rpm. The DNA pellet was washed once with 500 µl of 70% ethanol, then air-dried and resuspended in 100 µl TE (10 mM Tris pH 8.0, 1 mM EDTA).

Annealing of the seven oligonucleotides yielded the artificial gene sequence provided above as SEQ ID NO:1, which translate into the artificial protein (amino acid sequence) set forth above as SEQ ID NO:2. The annealed DNA was then used for cloning into HindIII and BamHI sites of the plasmid pUCNLSTBP1 (SEQ ID NO:11), illustrated in FIG. 3.

The foregoing is illustrative of the present invention and is not to be construed as limiting thereof. The invention is defined by the following claims, with equivalents of the claims to be included therein.

---

That which is claimed is:

1. A synthetic nucleotide sequence encoding the *Escherichia coli* LexA DNA binding domain having the amino acid sequence of SEQ ID NO: 2, wherein the synthetic nucleotide sequence comprises at least one codon that is modified from the *Escherichia coli* nucleotide sequence to optimize usage in an Arabidopsis species.

2. The synthetic nucleotide sequence according to claim 1, wherein over 50% of the codons of the sequence are optimized for usage by an Arabidopsis species.

3. The synthetic nucleotide sequence according to claim 1, wherein over 80% of the codons of the sequence are optimized for usage by an Arabidopsis species.

4. The synthetic nucleotide sequence according to claim 1, wherein the nucleotide sequence has the sequence set forth in SEQ ID NO:1.

5. The synthetic nucleotide sequence according to claim 1, wherein all of the codons are optimized for usage in *Arabidopsis thaliana*.

6. A DNA construct comprising the synthetic nucleic acid sequence of claim 1.

7. The DNA construct according to claim 6, wherein the synthetic nucleic acid sequence has the sequence of SEQ ID NO:1.

8. The DNA construct according to claim 6, further comprising a heterologous nucleic acid sequence and a polynucleotide encoding a transcription activator domain, wherein the heterologous nucleic acid sequence comprises the sequence set forth in SEQ ID NO: 10.

9. A plant cell comprising the DNA construct of claim 7.

10. A plant comprising the DNA construct of claim 8.

11. The plant cell according to claim 9, wherein the plant cell is a dicot cell.

12. The plant cell according to claim 11, wherein the dicot cell is an *Arabidopsis thaliana* cell.

13. A transgenic plant comprising the plant cell of claim 9.

14. The transgenic plant according to claim 13, wherein the plant is a dicot.

15. The transgenic plant according to claim 14, wherein the plant is an *Arabidopsis thaliana* plant.

16. A transgenic seed produced by the plant of claim 13.

17. A transgenic seed produced by the plant of claim 14.

18. A transgenic seed produced by the plant of claim 15.

19. A method of increasing the transcription of a heterologous gene in a plant or plant tissue comprising:

transforming the plant or plant tissue with a heterologous gene, a polynucleotide encoding a transcription activator domain, and the synthetic nucleotide sequence of claim 1, wherein the heterologous gene comprises the sequence set forth in SEQ ID NO: 10.

20. The method according to claim 19, wherein the plant is an *Arabidopsis thaliana* plant, and the synthetic nucleotide sequence has the sequence set forth in SEQ ID NO:1.

21. A synthetic nucleotide sequence encoding the LexA DNA binding domain, comprising at least one codon optimized for usage by an Arabidopsis species, wherein the nucleotide sequence has the sequence set forth in SEQ ID NO:1.

22. A DNA construct comprising the synthetic nucleic acid sequence of claim 21.

23. A plant cell comprising the DNA construct of claim 22.

24. The plant cell according to claim 23, wherein the plant cell is a dicot cell.

25. The plant cell according to claim 24, wherein the dicot cell is an *Arabidopsis thaliana* cell.

* * * * *